(12) United States Patent
Larkin et al.

(10) Patent No.: US 8,976,353 B2
(45) Date of Patent: Mar. 10, 2015

(54) MULTIWELL PLATE LID FOR IMPROVED OPTICAL MEASUREMENTS

(75) Inventors: Michael I. Larkin, Santa Barbara, CA (US); Amy D. Hanlon, Santa Barbara, CA (US); Daniel I. Some, Santa Barbara, CA (US); Richard J. Sleiman, Buellton, CA (US); David N. Villalpando, Lompoc, CA (US)

(73) Assignee: Wyatt Technology Corporation, Santa Barbara, CA (US)

( * ) Notice: Subject to any disclaimer, the term of this patent is extended or adjusted under 35 U.S.C. 154(b) by 0 days.

(21) Appl. No.: 13/492,527

(22) Filed: Jun. 8, 2012
(Under 37 CFR 1.47)

(65) Prior Publication Data

US 2013/0176556 A1    Jul. 11, 2013

Related U.S. Application Data

(60) Provisional application No. 61/495,839, filed on Jun. 10, 2011.

(51) Int. Cl.
| | |
|---|---|
| *G01N 21/00* | (2006.01) |
| *G01N 21/01* | (2006.01) |
| *G01N 21/51* | (2006.01) |
| *G01N 21/03* | (2006.01) |
| *G01N 21/25* | (2006.01) |

(52) U.S. Cl.
CPC ............... *G01N 21/01* (2013.01); *G01N 21/51* (2013.01); *G01N 21/0303* (2013.01); *G01N 21/253* (2013.01)
USPC .......................................... 356/338; 356/337

(58) Field of Classification Search
CPC ........ B01D 15/34; B01D 15/08; B01D 15/26; B01D 15/265; B01D 15/325; G01N 30/02; G01N 15/0205; G01N 2015/0288; G01N 2015/0294; G01N 2030/324; G01N 2030/625; G01N 21/253; G01N 21/51; G01N 21/532
USPC ......... 356/337–343, 39, 244; 250/208.1, 221, 250/458.1–467.1, 239, 559.4, 216, 227.25; 359/398; 215/307; 422/939; 435/288.4, 435/288.3, 305.3, 305.4, 287.2, 283.1, 435/287.1, 305.1; 436/165, 177, 178, 809
See application file for complete search history.

(56) References Cited

U.S. PATENT DOCUMENTS

| | | | |
|---|---|---|---|
| 6,258,325 B1 * | 7/2001 | Sanadi ........................ | 422/549 |
| 6,534,014 B1 | 3/2003 | Mainquist et al. | |
| 7,309,603 B2 | 12/2007 | Ma et al. | |
| 7,332,328 B2 | 2/2008 | Webb et al. | |
| 7,371,348 B2 | 5/2008 | Schleifer et al. | |
| 7,989,755 B2 * | 8/2011 | Sonehara et al. ............. | 250/216 |
| 2007/0210269 A1 | 9/2007 | Sonehara et al. | |

* cited by examiner

*Primary Examiner* — Tri T Ton
(74) *Attorney, Agent, or Firm* — David N. Villalpando; Philip J. Wyatt

(57) ABSTRACT

A lid for multiwell plates, allowing improved optical measurement of liquid samples within its wells, while mitigating evaporation from said samples, is disclosed. A surface element protrudes from the bottom of the lid into the fluid within a well. The protruding element may be hollow or solid such that light directed into the element may act to capture or direct the beam while preventing backscatter from reaching one or more detectors. The protruding element may direct the beam from the well without requiring the beam to pass through a fluid/air interface. The angle and shape of the lid surfaces and/or light absorbing/blocking colorization may be employed to minimize or eliminate back reflection. Evaporation is controlled by physically capping the well with the lid, either sealing against the face at the top of the well or the inside surface of the well.

16 Claims, 13 Drawing Sheets

MULTIWELL PLATE LID FOR IMPROVED OPTICAL MEASUREMENTS

PRIORITY

This application claims priority to U.S. Provisional Application No. 61/495,839, filed Jun. 10, 2011, "Multiwell measurement plate lid for improved optical measurements."

BACKGROUND

Light scattering is a non-invasive technique for characterizing macromolecules and a wide range of particles in solution. The two types of light scattering detection frequently used for the characterization of macromolecules are static light scattering (SLS) and dynamic light scattering (DLS).

Static light scattering is also known as multi-angle light scattering (MALS). SLS experiments involve the measurement of the absolute intensity of the light scattered from a sample in solution. This measurement allows the determination of the size of the sample molecules or particles, and, when coupled with knowledge of the sample concentration, allows for the determination their weight average molar mass. In addition, nonlinearity of the intensity of scattered light as a function of sample concentration may be used to measure interparticle interactions and associations.

Dynamic light scattering is also known as quasi-elastic light scattering (QELS) and photon correlation spectroscopy (PCS). In a DLS experiment, time-dependent fluctuations in the scattered light signal are measured using a fast photodetector. DLS measurements determine the diffusion coefficient of the molecules or particles, which can in turn be used to calculate their hydrodynamic radius.

Extensive literature has been published describing methods for making both static and dynamic light scattering measurements in flowing and batch (non-flowing) systems. See, for example, P. J. Wyatt, "Light scattering and the absolute characterization of macromolecules," *Analytica Chimica Acta*, 272, 1-40, (1993). With the development and improvement in the optical quality of multiwell plates, it has become possible to make both SLS and DLS measurements directly from samples contained therein. Methods capable of measuring samples directly in these multiwell plates are generally desirable given both the high-throughput nature of the measurements and the reduced sample volume requirements. Standard multiwell plates have 96, 384, or 1536 wells, each well is able to contain a different, distinct sample, and all wells may be tested in a single data collection run. In addition, use of these plates obviates the laborious need to clean and dry individual scintillation vials or cuvettes after each measurement. These plates generally have very low volume wells, and commercially available multiwell plate based measurement instruments are capable of light scattering measurements from sample volumes of 1 µL or less. These tiny sample volumes are of great benefit when a limited amount of sample is available from which to make measurements, particularly when compared to the 300 µL or larger sized measurement volumes often required by other light scattering techniques.

Multiwell plates, however, suffer from three primary issues which can make both DLS and SLS measurements difficult to perform in the wells themselves and may produce unreliable results. These issues are: 1) high background signal originating from sidewalls and other interfaces, 2) non-uniformity of the fluid meniscus shape and level from well to well, and 3) evaporation.

The deleterious effects of high background signal, or noise, is caused by light scattered from anything other than the sample. This background signal decreases the light scattering instrument's sensitivity due to the increase in the noise present in relation to the useful signal scattered from the sample itself, and therefore an overall reduction in the signal-to-noise ratio upon which the sensitivity of the measurement is dependent. High background is primarily due to scattering from interfaces traversed by the light beam and secondary scattering of interface flare from sidewalls and other surfaces present in a multiwell scattering measurement. It is an objective of this invention to minimize the number of surfaces which the beam traverses likely to result in background scatter. For DLS measurements, higher sample concentrations of valuable sample materials are generally required to overcome this background signal. A further objective of this invention is that by the mitigation of background scatter, DLS measurements may be performed at lower concentrations than have been possible heretofore.

Non-uniformity of the fluid meniscus shape from well to well causes variability in the background signal. FIG. 1 shows a simple ray diagram in a single well for a conventional DLS measurement in a multiwell plate such as that performed by many DLS plate readers, such as the DynaPro® Plate Reader (Wyatt Technology Corporation, Santa Barbara, Calif.). FIG. 2 illustrates several wells of the same multiwell plate. Note that the shape of the meniscus 1, i.e., liquid/air interface, shown in FIG. 2 may vary from well to well. This variation can result in non-uniform angles of refraction and reflection from well to well of which can result in significant changes in the intensity of backscatter and secondary scatter observed by the detector. It is an objective of the invention to control the shape of the interface through which the beam departs the sample.

Evaporation can alter the sample state, skew results through altered background intensity, or prohibit light scattering measurement entirely. Partial evaporation of the solvent from a well increases the concentration of the dissolved solute which may have deleterious effects on the sample itself. Evaporation can also impact the meniscus curvature as discussed above as well as meniscus height in the well. More substantial evaporation of the sample solvent can often completely prevent accurate measurement, which is a problem particularly prevalent in very small volume multiwell plates where even a small amount of evaporation results in a large change in the height of the fluid level. Even for the larger sample volumes contained in 96 well plates, evaporation concerns prevent often useful extended measurement times as well as measurements at elevated temperature, thus making studies of temperature dependence exceedingly difficult. It is a further objective of this invention to minimize evaporation from multiwell plates.

These limitations disclosed above seriously inhibit the accurate collection of light scattering data from samples contained within the wells of multiwell plates. Means are necessary to mitigate evaporation from liquid samples contained in the wells, to increase the uniformity of background light scatter from well to well, and to reduce the intensity of background light measured by the detector. A primary objective of the present invention is to provide means by which all of these limitations for using multiwell plates for optical measurements may be mitigated allowing for an increased quality of optical measurements of samples contained in multiwell plates that have been impossible prior to the presently disclosed invention.

BRIEF DESCRIPTION OF THE INVENTION

In order to overcome the limitations to quality measurements described above, a new type of lid structure for multiwell plates is disclosed. The various embodiments of the inventive structure control evaporation, increase well to well uniformity in background signal, and reduce background signal overall. In addition the lid structure may be manufactured in such a way as to allow it to operate universally with multiwell plates produced by any number of manufacturers by means of adaptive physical barriers that may also aid in preventing evaporation.

The primary feature in all embodiments of the invention is a surface which projects into the fluid contained within a well. In one embodiment this surface may be an opaque hollow tube into which the beam of light is directed. This tube acts to capture the beam and may be oriented such that the beam exits the fluid prior to making contact with the sidewall of the tube. The tube extending into the fluid prevents back scatter from the point of contact with the post or the air/lid interface from reaching the light scattering detector or detectors. Alternatively, the surface projecting into the fluid contained in the well may also be a solid, transparent or partially transparent post that acts to direct the beam out of the well in such a way as to cause minimal unwanted scatter by, in part, allowing the light to exit the liquid sample without traversing a fluid/air interface. In addition, the end surface of the post may be angled to minimize back-reflection from the liquid/post interface, control the direction of the reflected and transmitted light, and inhibit bubble collection on the solid face of the post. The surface of the lid structure may also have areas of either light-absorbing or light-blocking colorization to prevent back reflection and secondary scatter from reaching the detector or detectors.

To prevent evaporation from the wells of the multiwell plate, an adhesive layer may be incorporated to seal the lid to a plate surface. Alternatively, a flexible physical barrier may also be incorporated to provide a seal between the lid and a plate surface without the use of an adhesive.

DETAILED DESCRIPTION OF THE INVENTION

Figure 1:
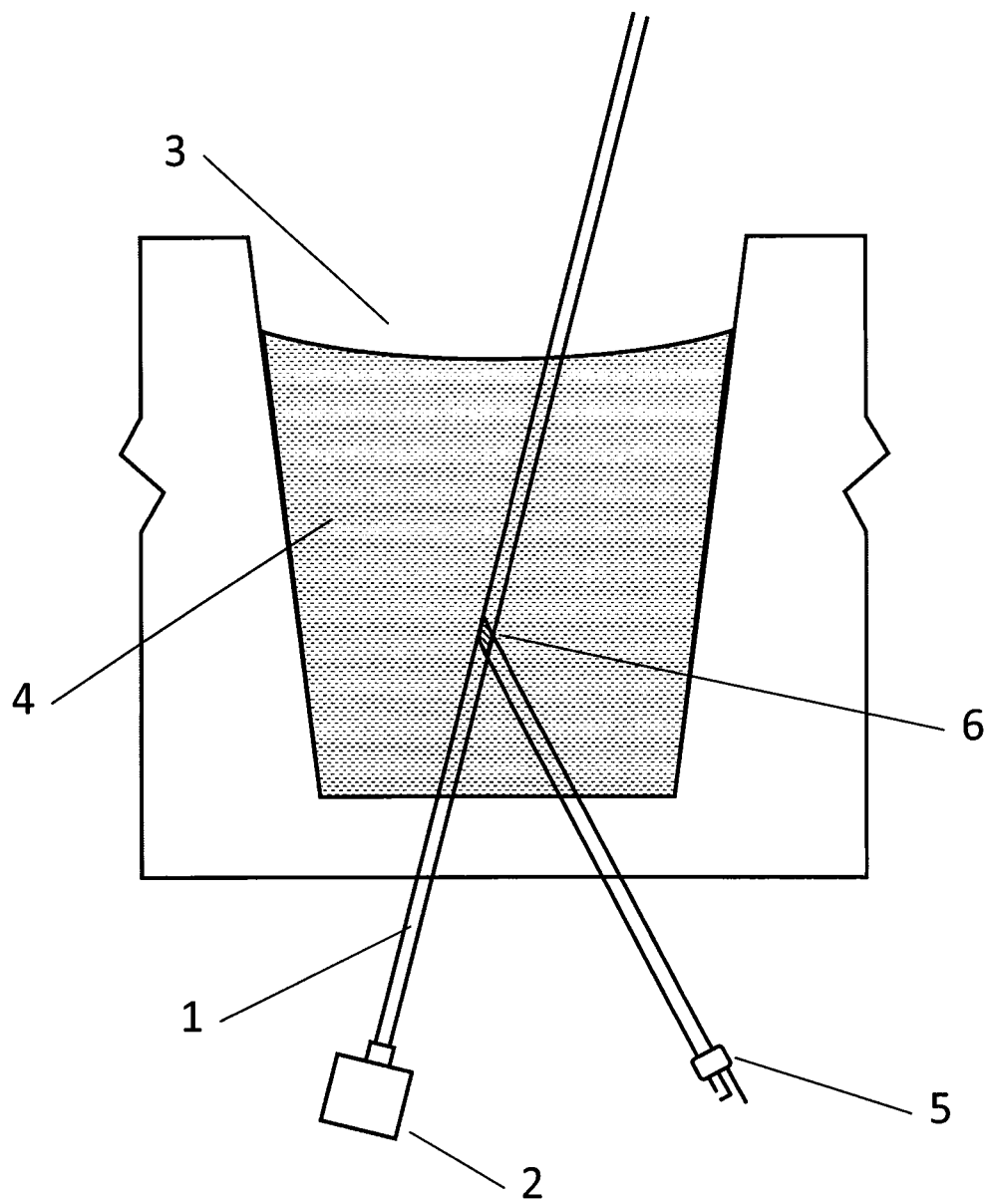
FIG. 1 illustrates a conventional light scattering measurement from a single well of a multiwell plate.

FIG. 1 illustrates how a conventional light scattering measurement is made within a single well of a multiwell plate. In this depiction a beam of light 1 is emitted by a light source such as a laser 2 and is transmitted through the well 3 of a multiwell plate partially filled with a sample containing fluid 4. A detector 5 gathers scattered light from the measurement volume 6, which consists of the region of intersection between the light beam and the area subtended by the field of view of the detector 5. In the case of a SLS measurement, the detector is generally a photodiode. For DLS measurements the detector is a photon counting module such as an avalanche photodiode (APD) or a photomultiplier tube (PMT). As discussed previously, light scattered or reflected from any of the interfaces may reach the detector or cause significant backscatter and lead to erroneous results.

Figure 2:
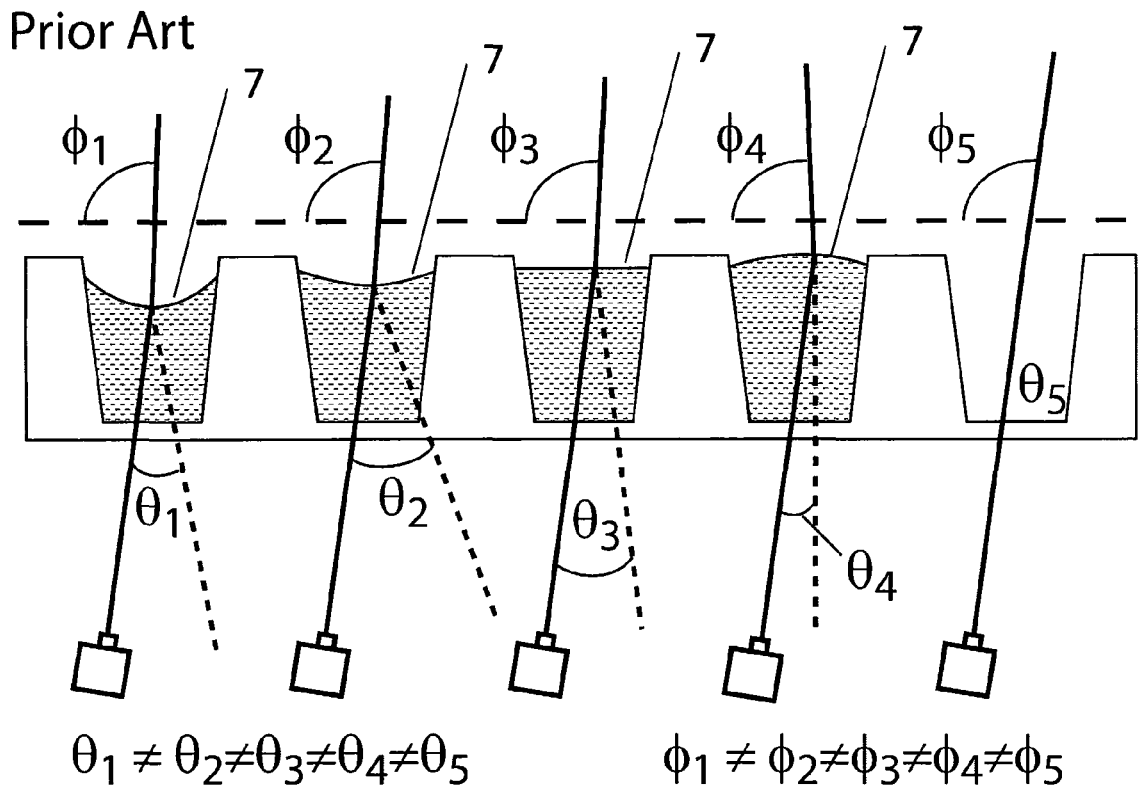
FIG. 2 shows the variance of refraction and reflection of a beam due to the shape of the meniscus of the fluid in a multiwell plate.

As previously discussed the shape of the meniscus 7 at the fluid/air interface can affect both the angle of reflection ($\theta$) and refraction ($\phi$) of the beam as it exits the fluid as shown in FIG. 2. This example illustrates the varying path and length of the reflected beam as it traverses the cell from the liquid/air interface. This results in significant changes in the intensity of backscatter and secondary scatter observed by the detector. The radius of curvature is dependent on several variables including the fluid surface tension, sidewall material, and fluid depth. Non-uniform background is particularly detrimental in SLS measurements, which require a uniform background so that the scattering intensity from the sample alone in each well may be accurately determined. Even small differences in background intensity can significantly alter SLS results. Further, the angle $\phi$ of the refracted beam is greatly affected by the shape of the meniscus, making it difficult to predict the position of the beam after it has traversed the fluid sample, thereby reducing the effectiveness of any desired measurement based on the transmitted beam. In order to rectify this source of non-uniformity, it is highly desirable to control the shape of this liquid air interface or eliminate the need for the beam to traverse it.

Figure 3:
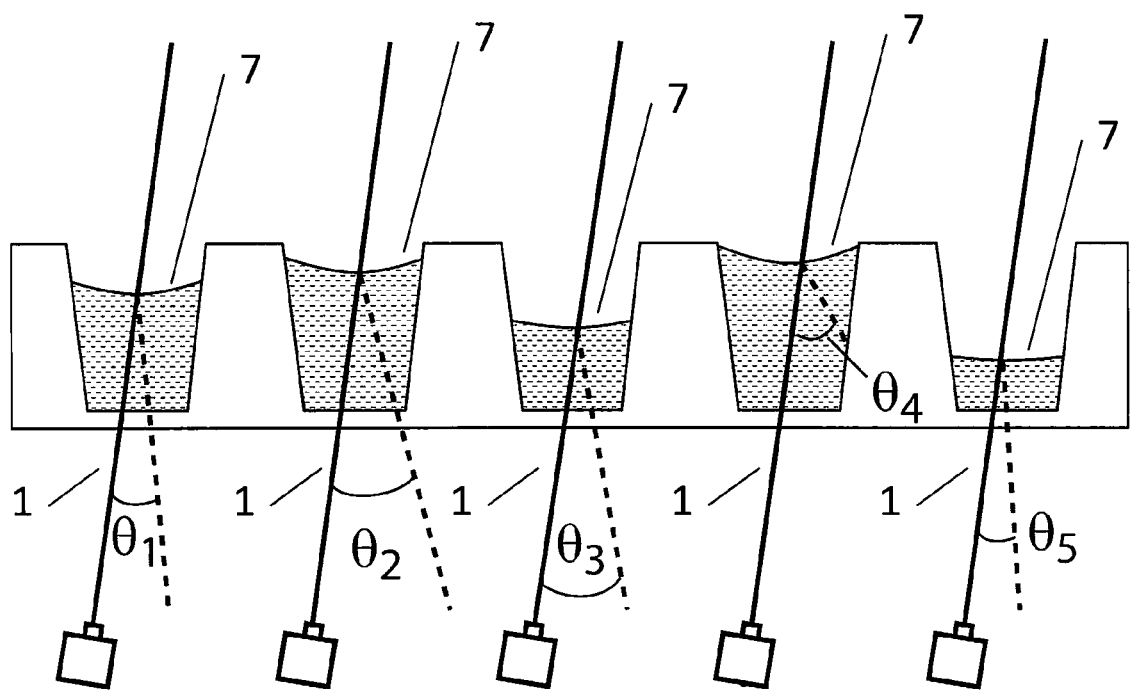
FIG. 3 shows the variance of refraction and reflection of a beam due to varying levels of height of sample evaporation within wells of a multiwell plate.
Figure 4:
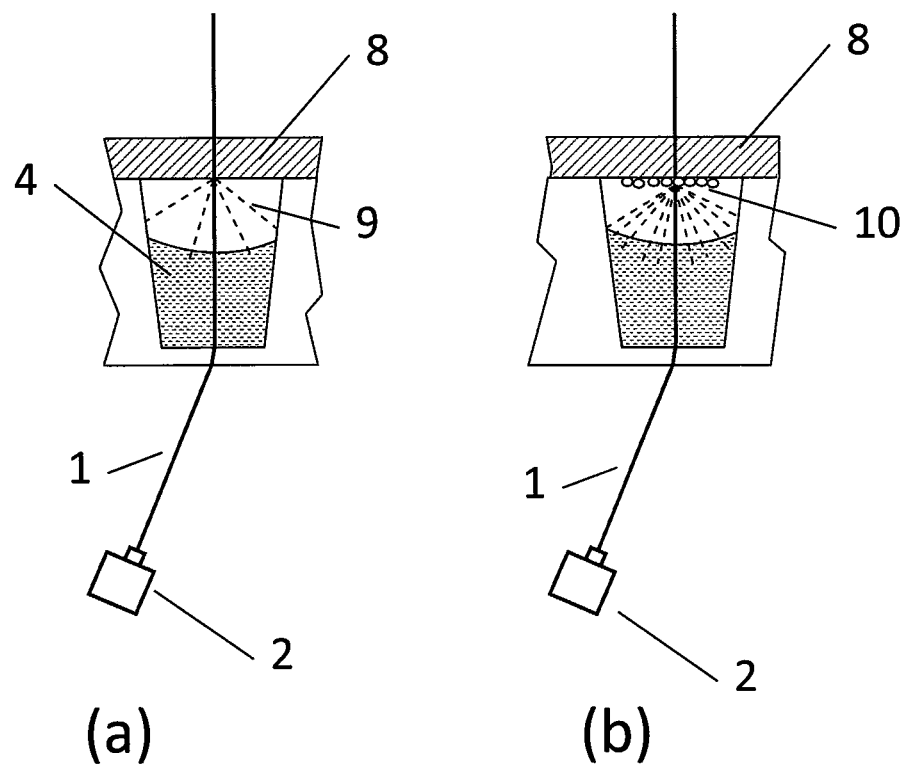
FIG. 4 shows an abbreviated cross section of a multiwell plate capped with a standard lid with a) no condensation and b) condensation droplets formed on the lid.

FIGS. 3 and 4 indicate some of the problems associated with evaporation when performing light scattering measurements in a well plate. As discussed previously, the well fluid meniscus 7 will often vary in height from well to well as a result of evaporation. Non-uniformity in fluid level height can occur due to inconsistency in the filling of the wells. These divers levels will cause the direction of light reflected from the fluid/air interface to vary from well to well, causing differing values of background scatter.

In the past, evaporation from well plates has been addressed primarily by either a film or cover placed on the surface of the plate above the sample wells, or a layer of oil overlaying the sample contained in each well. However, for light scattering measurements, both of these commonly used evaporation mitigation techniques can be problematic. Films and solid transparent covers can promote significant backscatter from the interface of the exiting light beam with the lid or film. As illustrated in FIG. 4a, the beam 1 from a laser source 2, after traversing the sample containing well 4 is incident directly upon the air/surface interface of the multi-well plate cover 8. Backscatter 9 generated from the beam striking the cover can have deleterious effects on any light scattering measurement, as discussed previously. Additionally, fluid contained in the wells may evaporate and condense on the inner surface of the film or cover, as shown in FIG. 4b. This layer of condensation 10 is highly scattering and is generally non-uniform from well to well. Again, the backscatter intensity may overwhelm sample signal, greatly decreasing the sensitivity of the measurement, and often leading to erroneous results. While the use of an oil overlay eliminates the issue of condensation, the potentially negative interactions of oil and sample molecules are well known, as documented in the 2004 article by L. S. Jones et al, "Silicone oil induced aggregation of proteins," published in the Journal of Pharmaceutical Sciences, volume 94, pages 918-927. Such unintended interactions may result in an inaccurate representation of the true sample characteristics, and may occur without the knowledge of the experimenter. In addition, oil overlays can be difficult and time consuming to apply to each sample containing well. The practical requirement of such an oil overlay to control condensation prevents many users from attempting multiwell plate-based light scattering measurements. The present invention obviates the need to use an oil overlay to control evaporation while also ruling any deleterious effects scattering due to condensation.

The present invention, in its many embodiments, addresses each of the problems associated with conventional light scattering measurements performed in multiwell plates described above. However, inasmuch as experimental conditions may vary when making multiwell plate measurements, for example, in an experiment which will be made quickly, evaporation may not be a concern, therefore a particular embodiment which mitigates problems associated with variable liquid-air interfaces may be employed which do not necessarily also mitigate evaporation. All embodiments of the present invention comprise a lid structure to be fitted onto a multiwell plate. This lid comprises a surface which projects in to the fluid contained within the well. Various embodiments of these surfaces may be referred to as posts (when solid) or tubes (when hollow) throughout the remainder of the specification. It should be noted that said lid need not necessarily be of a nature to cover the entire well plate, nor provide posts or tubes extending into each well; rather a small strip may serve adequately as a lid for a row or column of wells within the multiwell plate. Indeed, even a small section encompassing a handful of wells, or even a single well would be considered a lid for purposes of this disclosure.

Figure 5:
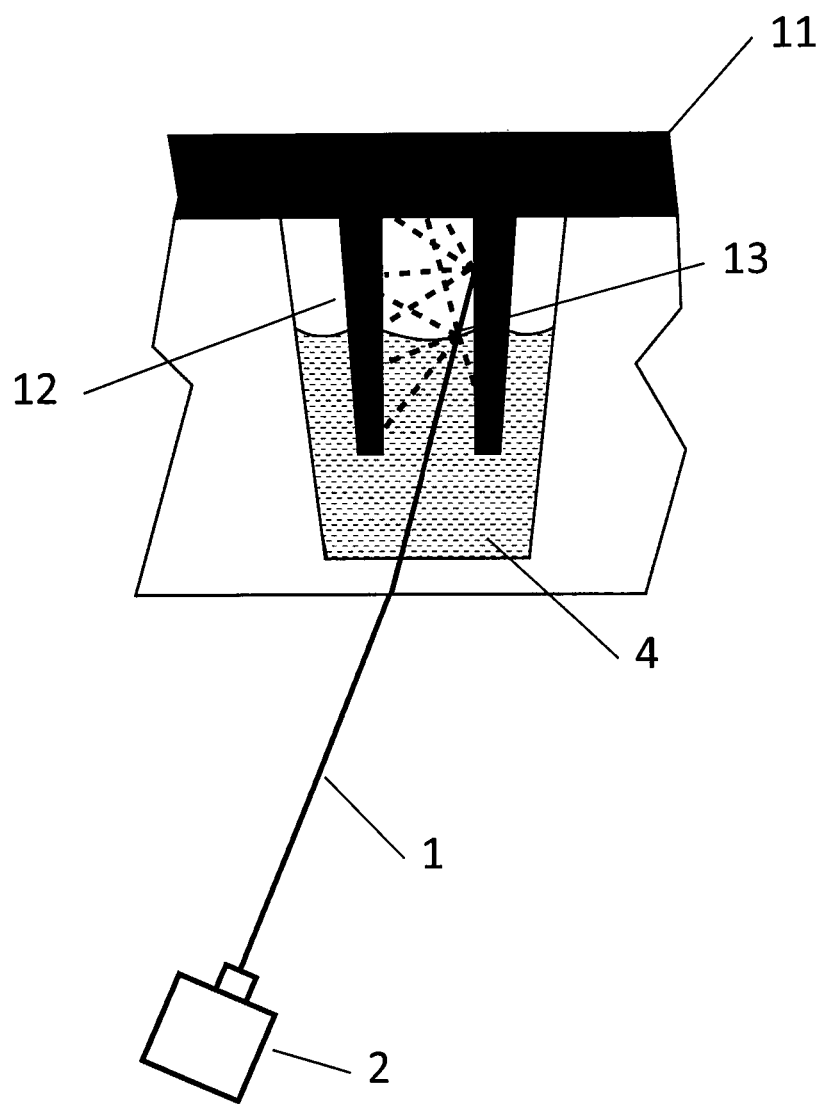
FIG. 5 shows a hollow "beam capture" surface projecting into the fluid of the well according to an embodiment of the present invention.

One embodiment of the inventive lid structure comprises a hollow tube design shown in cross section in FIG. 5. In this embodiment, the lid structure 11 is made of an opaque, non-reflective surface, such as a matte black polymer. The beam 1 enters the hollow tube 12, and, after exiting the fluid 4, intersects the inner surface of the light absorbing tube. In some cases where a high powered laser is used as a light source, the beam may be intense enough to melt or burn plastic and non-submersion of the point of incidence in air reduces the likelihood of sample contamination by the products of lid degradation. For this structure, as the beam exits the sample there are two points of back reflection or background scattering: the liquid/air interface 13, and the point where the beam intersects the inner surface of the tube. The tube 12 extended into the sample fluid shields the detector from both sources of background light. In this manner, the laser and background light are both "captured" by the inventive lid.

Figure 6:
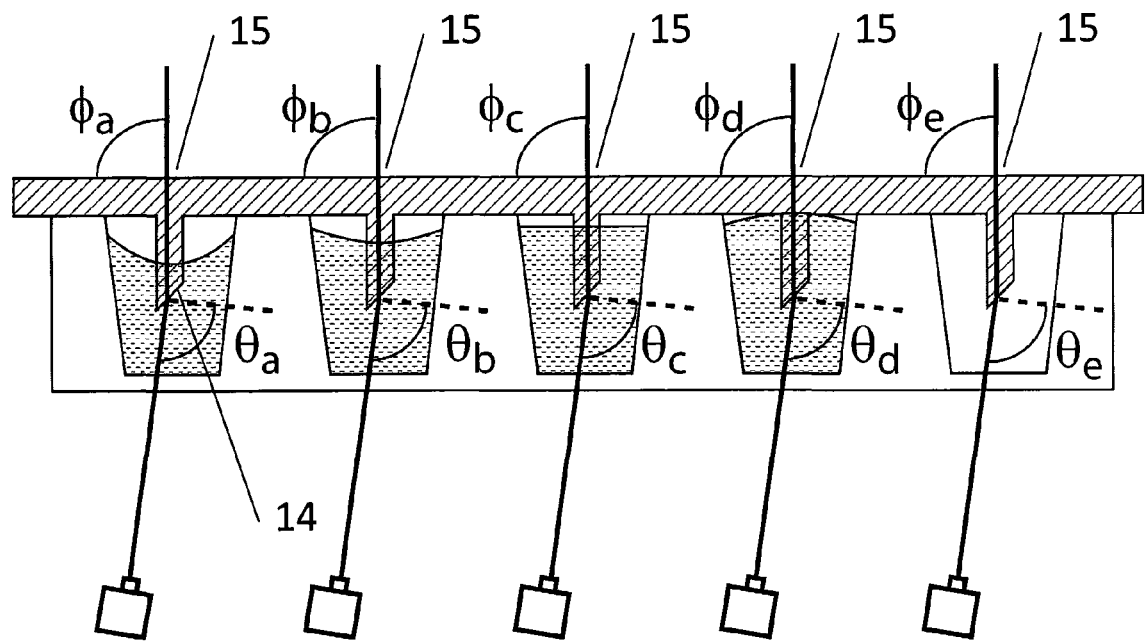
FIG. 6 shows an embodiment of the present invention wherein solid posts project into the sample contained within the well with the surfaces so configured as to control reflection and refraction of the transmitted beam.

As illustrated in FIG. 6, the surface projected into the fluid of the well may also be a solid post. This post may be either transparent or partially transparent. In this embodiment, as the incident surface 14 of the solid post is submerged, and therefore fully wetted, condensation cannot form thereon, thus eliminating a potential source of back scatter. The beam incident surface of the post may be angled in order to decrease the likelihood of the adhesion of bubbles to this critical surface. In addition, this angled surface also serves to disperse bubbles during centrifugation, which is a commonly performed practice prior to measurement. A further advantage of an angled incident surface is its ability to direct any light reflected from the liquid/lid interface in a desired direction, e.g. away from a surface which is observed by the photodetector. Further, the amount of reflected light may be minimized by constructing the angled surface to take advantage of Brewster's angle, as discussed in the following paragraph. For linearly polarized light, the amount of light reflected from that interface can theoretically be eliminated by properly choosing the angle and orientation of the angled surface.

Figure 7:
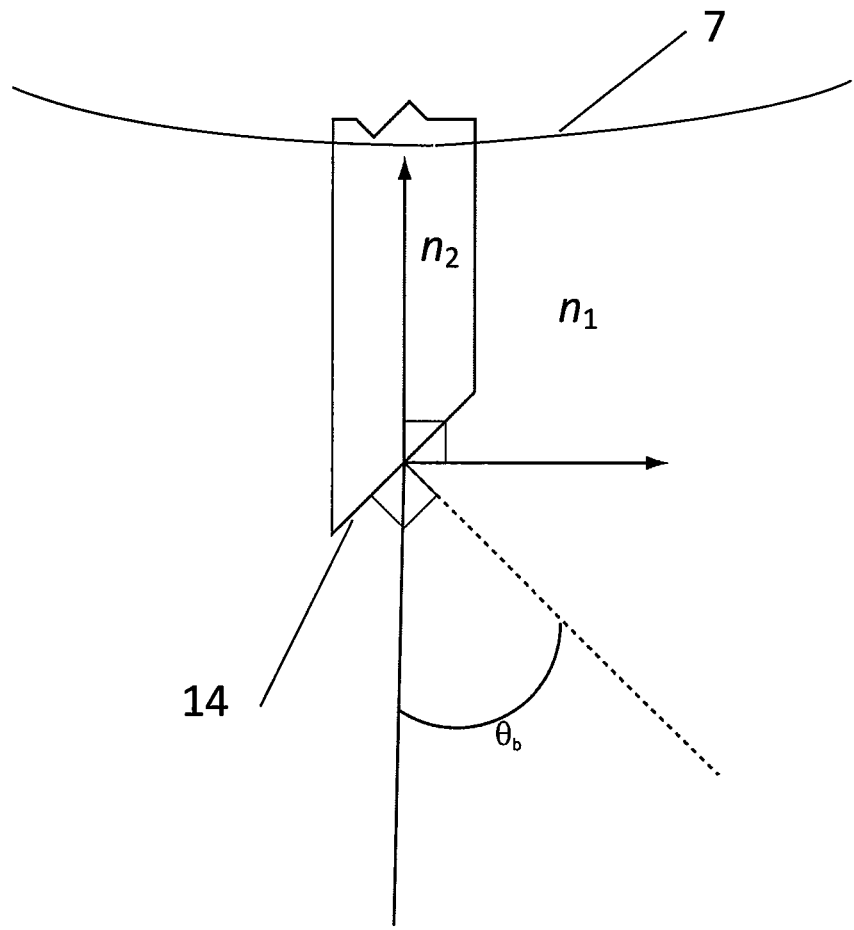
FIG. 7 is a representation of a solid post embodiment of the present invention utilizing Brewster's angle to control the transmitted beam.

Brewster's angle refers to the particular angle of incidence for which light of a certain polarization is not reflected at all, but rather is completely transmitted. To utilize this phenomenon, the incident light must be p-polarized, such that the light has an electric field vector parallel to the plane of incidence, being the plane containing the incident, transmitted, and reflected rays, as shown in FIG. 7. Brewster's angle ($\theta_B$) is defined as $\theta_B = \tan^{-1}(n_2/n_1)$, where $n_1$ is the index of refraction of the solvent in this case and $n_2$ is the index of refraction of the post. Taking this relationship into account, the incident surface 14 can be tuned to accommodate the specific refractive index of the lid material and the expected refractive index of the sample solution. As different sample solutions within individual wells in the same well plate may have different refractive indices, it may not be practical for the incident surface 14 in each well to be perfectly tuned to Brewster's angle. However, although the coefficient of reflection is theoretically zero only exactly at Brewster's angle, reflection is dramatically reduced for incident light which is close to Brewster's angle, say within about 10°, and the interface surface may be designed to have an angle as close as possible to Brewster's angle for the average refractive index of a range of likely samples.

Even in the absence of the interface surface at an angle near Brewster's angle, directing the beam to exit the fluid into a solid surface rather than into air reduces the amount of light which is back-reflected upon the beam crossing the interface, as at an interface of two materials the coefficient of reflection increases as the refractive index difference between these materials increases. For most cases, the refractive index difference between a sample solution and a solid such as plastic or glass is significantly less than the refractive index difference between a sample solution and air. For normal incident light on an interface, the intensity of reflected light may be expressed as $(n_1-n_2)^2/(n_1+n_2)^2$, where $n_1$ and $n_2$ are the refractive indexes of the initial and final materials, respectively. For example, the back reflected intensity of a water/air interface is 1.7% for normal incidence. For a lid material with a refractive index of 1.5, the back reflected intensity drops to 0.5%. Therefore, a liquid/lid interface will generally have less back reflection than the standard liquid/air interface.

Figure 8:
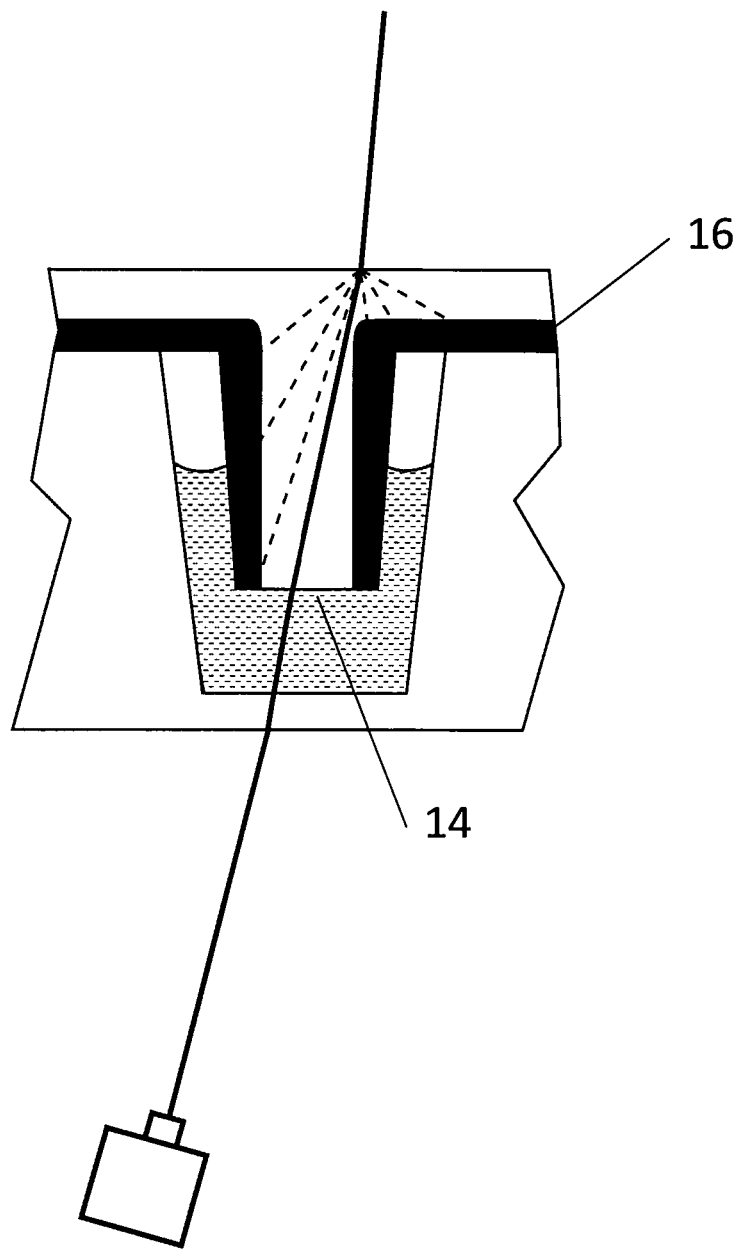
FIG. 8 illustrated an embodiment of the invention wherein the post is partially colorized about its perimeter.

The lid/air interface 15, as shown in FIG. 6, however, can still cause significant issues, as back reflection for normal incidence at this interface is predicted to be 4% for a typical sample. Reducing the reflection at the liquid/lid interface 14 may not be helpful if concurrently the reflection at the lid/air interface is substantially increased. To this end, the lid material may incorporate light absorbing or light blocking colorization to reduce background light observed by the detector. One embodiment of the lid structure shown in FIG. 6 is made of a transparent polymer imbued with a dye that absorbs light at the wavelength of the incident beam. As discussed earlier, laser beams commonly used in current measurement systems may be powerful enough to melt and burn plastic in which the light is strongly absorbed, as would be the case if the lid was manufactured from a highly absorbing black polymer. However, the incorporation of a small amount of light absorbing dye into an otherwise transparent plastic allows the absorbed energy from the light beam to be distributed over a significant volume, thereby preventing the light from burning the lid while simultaneously preventing it from contributing to background scattering. The beam may transverse the lid without complete absorption, but backscattered light may be largely absorbed prior to reaching the sample. Alternatively, as depicted in FIG. 8, the non-beam transiting outer surfaces of the lid may also incorporate a light-blocking layer 16. In this manner, any back scatter from lid/air interface is blocked prior to reaching the detector. In addition, it is possible to have a thin film anti-reflection coating incorporated at the lid/air interface surface 15, which may reduce the reflected intensity to below ~0.2%.

Figure 9:
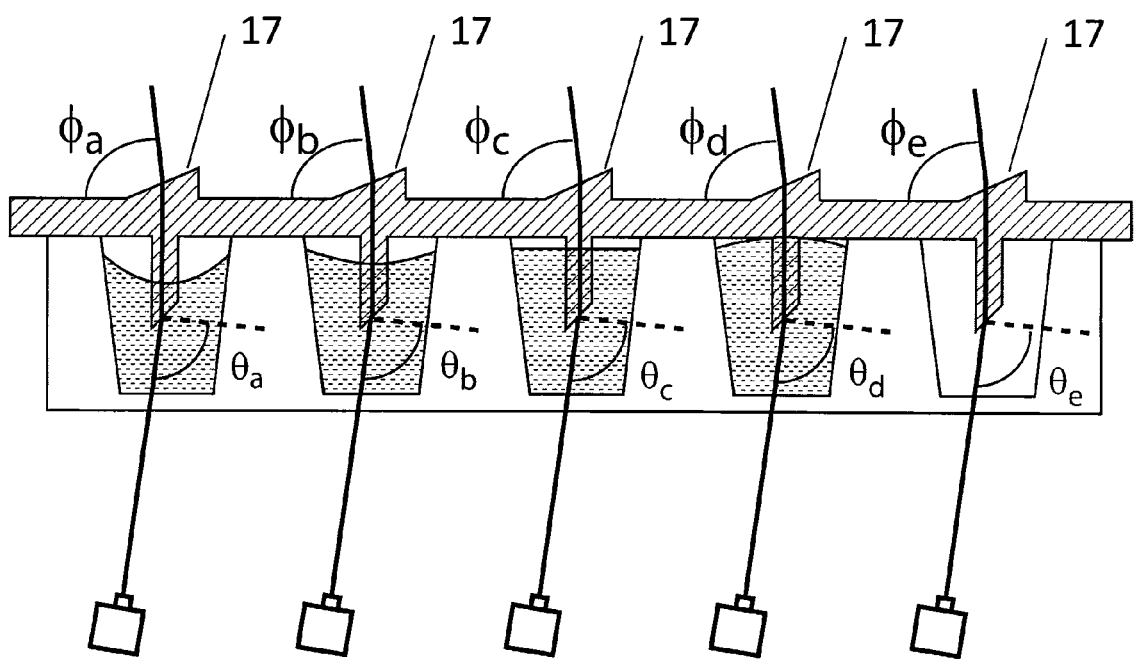
FIG. 9 shows an alternate embodiment of the top surface of the lid so designed as to control the beam transmitted and refracted at the lid/air interface.
Figure 10:
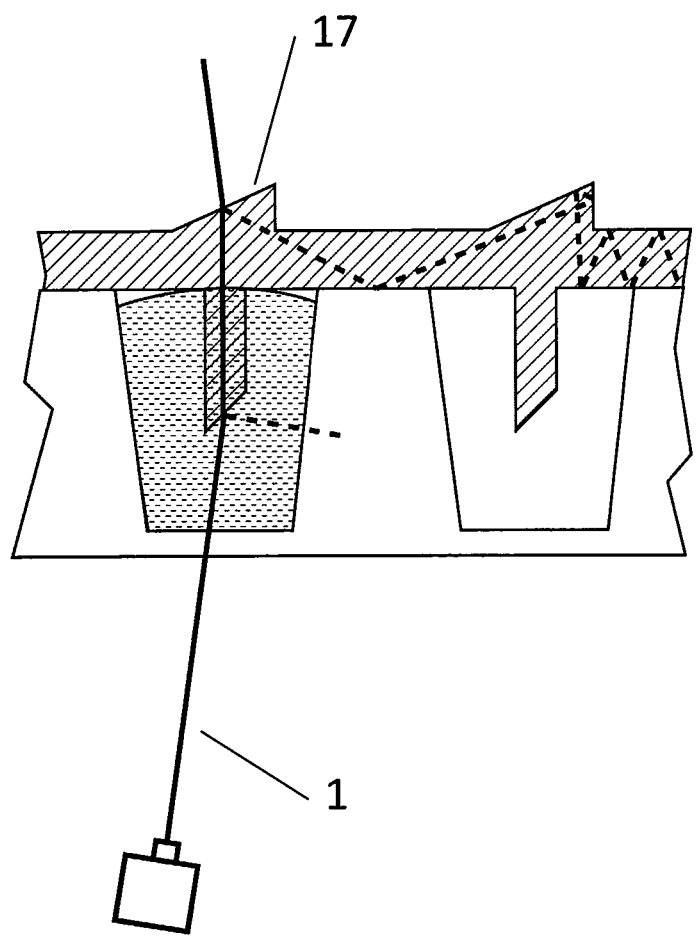
FIG. 10 demonstrates a possible ray trace of the path of a reflected beam of light at the lid/air interface for embodiment of lid structure shown in FIG. 9.

An additional embodiment for designs in which the beam passes completely through the lid includes angled structures 17 incorporated into the top surface designed to direct any back-reflected light away from the measurement volume as illustrated in FIG. 9. FIG. 10 shows an exploded view of this embodiment illustrating the path of the light beam 1 reflected from the lid/air interface of a single well by means of the light directing structure 17 incorporated into the top surface of the lid. Light reflected from the lid/air interface is directed away from the immediately surrounding wells. To aid in cost reduction and ease of manufacturing, as well as to improve mechanical stability, these light directing structures may be incorporated linearly across one or more entire rows or columns rather than constructed individually for each well.

Figure 11:
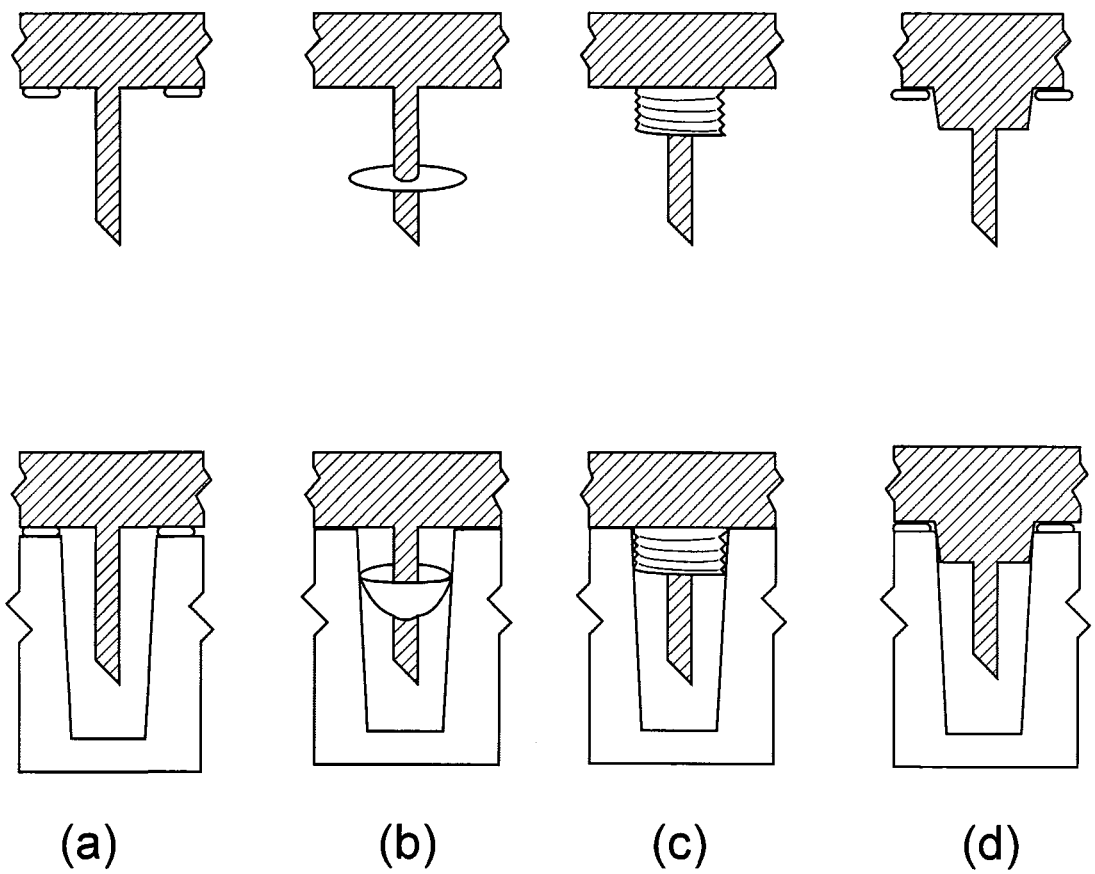
FIG. 11 shows several embodiments of the present invention by which evaporation may be controlled.

In order to decrease problems associated with solvent evaporation, the lid may be bonded to the outer rim of a well or wells using an adhesive surface, such as a pressure sensitive adhesive. This adhesive may be in contact with the post, or present only where the lid is expected to make contact with the well plate as shown in FIG. 11(a). As some users may prefer not to have an adhesive surface to come into contact with sample solutions, another method of preventing evaporation would involve the use of a flexible plastic portion of the lid, such as the self-adjusting flange shown in FIG. 11(b), which is pushed up to form a cone as the lid is installed. The angle of the cone depends upon the inner diameter of the well, allowing the flange to make physical contact with the well sidewalls regardless of the plate-to-plate well diameter variability.

An additional embodiment for improved evaporation control without the use of adhesive entails a cap, surrounding the post or tube, as shown in FIG. 11(c). The material of the cap would be flexible enough to enter and seal the well. As the placement of the plate within a centrifuge is a common technique used in the preparation of a multiwell plate for many optical measurement techniques, and a flexible cap may be significantly deformed in the centrifugation process, a solid shoulder in contact with the plate may be employed alternately. FIG. 11(d) shows such a lid with adhesive used to seal the post. This particular embodiment may also improve the alignment of the lid to the plate.

Figure 12:
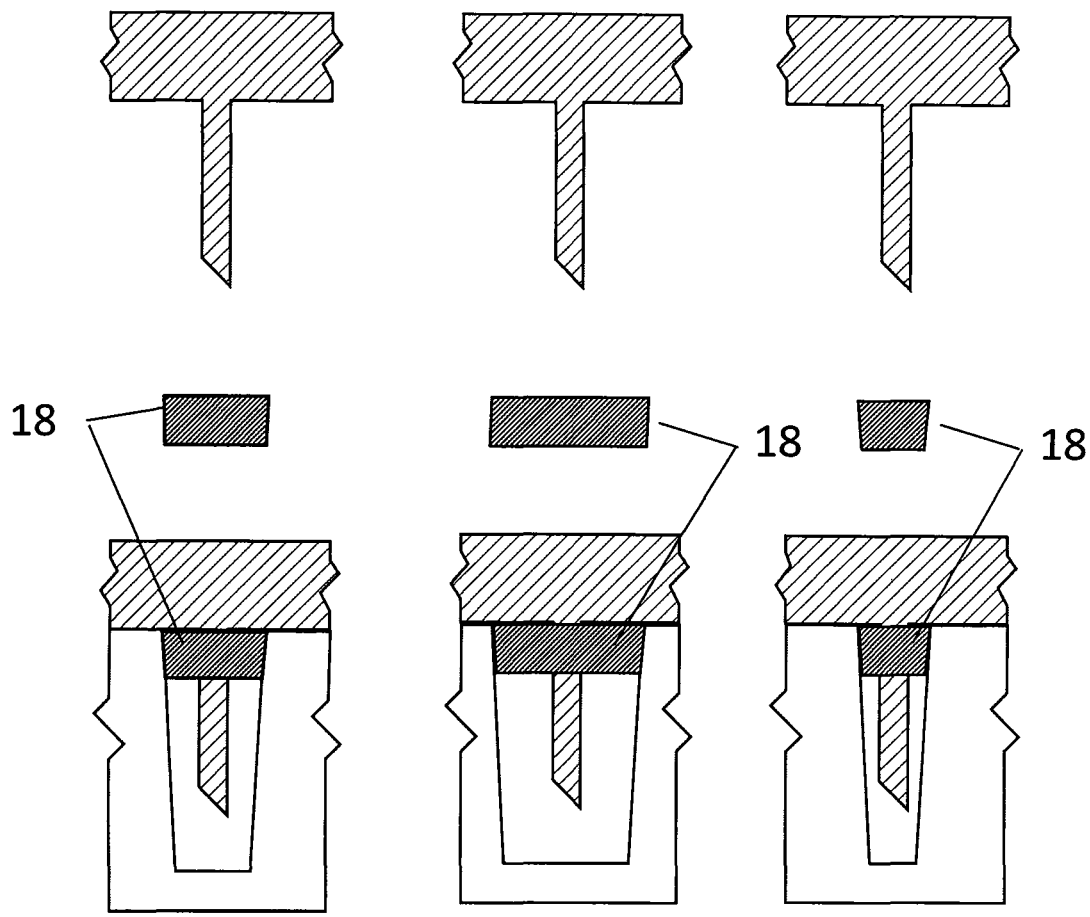
FIG. 12 shows demonstrations of several adaptive structures that mitigate evaporation and allow the inventive lid structure to be used with multiwell plates of varying configurations.
Figure 13:
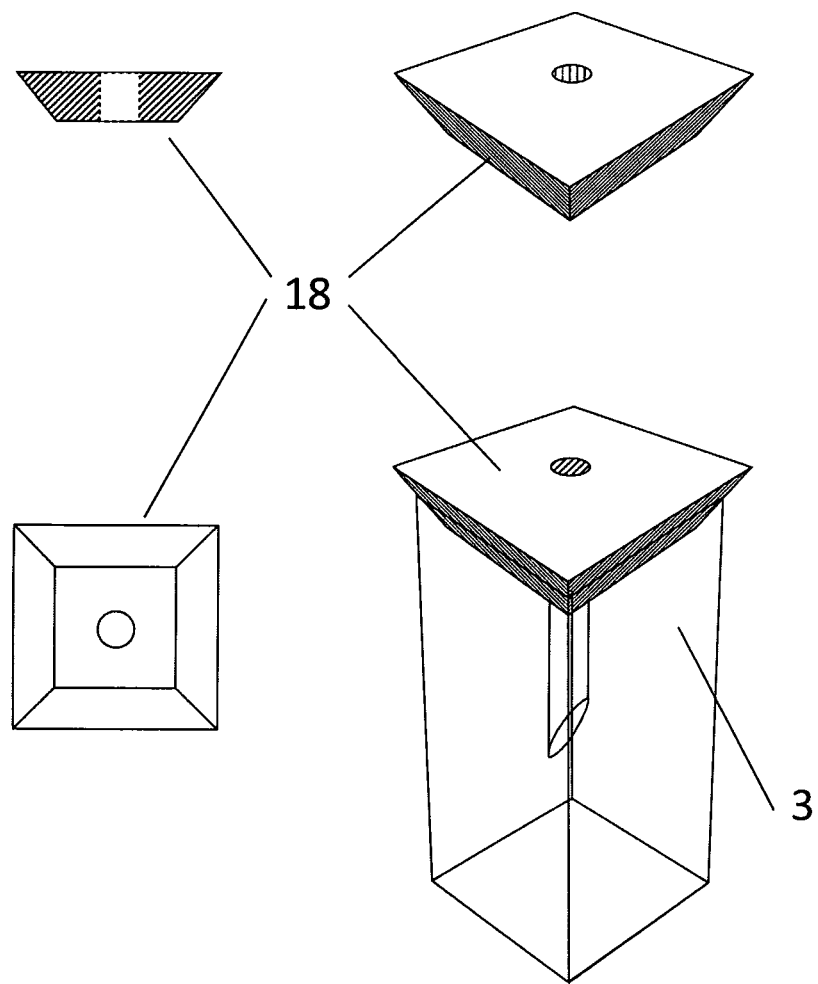
FIG. 13 shows several views of a specific embodiment of an evaporation control mechanism useable in conjunction with the inventive lid structure used in conjunction with a multiwell plate containing rectangular shaped wells.

As there are multiple manufacturers of multiwell plates with the same number of wells which may vary to small degrees in form, it will be advantageous to have a lid that may be used universally in conjunction with plates of the same number of wells supplied by different manufacturers. To this end, the evaporation control mechanism employed as part of the inventive lid structure can also serve as an adapter. In this embodiment one or more adaptive grommets 18 are placed around the projecting surface, solid post or hollow tube, of the lid structure. These grommets will vary in thickness and width, and will be used with a universal lid design. FIG. 12 illustrates how various adaptive grommets may be used to allow the multiwell plate lid to fit to and seal any number well conformations. Further, as with the embodiments shown in FIG. 11(b)-(d), when a flexible adaptor/sealer is used, the use of adhesive may be avoided by either including on the lid a clasping mechanism, thus providing it with a physical connection to the plate, or simply friction fitting the lid to the plate. An example of an adaptive grommet capable of allowing a cylindrically shaped solid post element of a lid capable of also controlling evaporation in a square shaped well is shown in FIG. 13.

It should be noted that, while throughout this disclosure, the benefits of the inventive lid structure have been demonstrated primarily by the use of examples relating to static and dynamic light scattering measurements, the utility of this invention should not be considered limited to light scattering applications. Indeed, any number of optical measurement techniques for samples contained in a multiwell plate may be improved by our inventive design including, but in no way limited to, the measurement of turbidity, absorption, fluorescence and refractive index. The absolute refractive index of a sample, for example, could be simply measured for any number of solutions contained in the wells of a multiwell plate through the use of one of the solid post embodiments of the invention by employing a split photodetector such as that used in standard refractive index detection systems, or photodiode array such as that employed by Larkin, et. al., in U.S. Pat. No. 7,283,221, issued Oct. 15, 2007, "Refractometer cell for both absolute and differential refractive index measurement of fluids," and incorporated herein by reference, located above the lid to measure the position of the transmitted beam emerging at the lid/air interface. Further, following calibration, such a system would enable the determination of the concentration of the samples contained within a given well by measuring the degree to which the beam transmitted through the top surface of the lid deviates from that of a well containing only solvent.

There are many embodiments of our invention that will be obvious to those skilled in the arts of measurement optics and evaporation control that are but simple variations of our basic invention herein disclosed that do not depart from the fundamental elements that we have listed for their practice; all such variations are but obvious implementations of the invention described hereinbefore and are included by reference to our claims, which follow.

The invention claimed is:

1. A multi-well plate lid, said lid being a removable or hinged cover for the top of said multi-well plate, for reducing evaporation from, while improving optical measurements of a plurality of liquid samples within the wells of a multiwell plate comprising
   A) a top surface;
   B) a bottom surface which rests on, or is seated above, the surface surrounding the openings of said sample containing wells; and
   C) a plurality of elements protruding from said lid bottom surface, each of said elements extending into an individual liquid sample containing well, wherein said protruding elements are arranged such that they may convey a light beam passing through said sample from below or entering said sample through said elements, wherein said protruding elements comprise solid posts which comprise
   a. an inner core comprising at least one a flat surface which is intersected by said light beam, said inner core being transparent or partially transparent at the wavelength of said light beam; and
   b. an outer circumferential surface which absorbs light at the wavelength of said light beam.

2. A multi-well plate lid, said lid being a removable or hinged cover for the top of said multi-well plate, for reducing evaporation from, while improving optical measurements of a plurality of liquid samples within the wells of a multiwell plate comprising
   A) a top surface;
   B) a bottom surface which rests on, or is seated above, the surface surrounding the openings of said sample containing wells; and
   C) a plurality of solid posts protruding from said lid bottom surface, wherein each of said solid posts
      a. extends into an individual liquid sample containing well,
      b. is arranged such that it may convey a light beam passing through said sample from below or entering said sample through said post,
      c. partially absorbs light at the wavelength of said light beam, and
      d. comprises a flat, angled surface through which said beam passes, said angled surface of said post selected to be within 10 degrees of Brewster's angle relative to the propagation direction and polarization of said light beam.

3. The lid of claim 1 wherein said inner core is transparent to the wavelength of said light beam.

4. The lid of claim 1 wherein said inner core partially absorbs light at the wavelength of said light beam.

5. The lid of claim 1 wherein said solid post comprises at least one flat surface, said flat surface is angled so as to minimize reflection of said light beam into said well.

6. The lid of claim 5 wherein said angled flat surface of said post is selected to be within 10 degrees of Brewster's angle relative to the propagation direction and polarization of said light beam.

7. The lid of claim 2 further comprising a shoulder element adjacent to said bottom surface and said solid post, wherein said shoulder element is angled such that a portion of it rests on the rim of said sample containing well and another portion of said shoulder protrudes into the sample containing well.

8. The lid of claim 2 wherein said top lid surface further comprises angled structures shaped to minimize any back reflection from the lid and air interface of said light beam passing through said solid post from passing back into said well.

9. The lid of claim 1 wherein said top lid surface further comprises angled structures shaped to minimize any back reflection from the lid and air interface of said light beam passing through said solid post from passing back into said well.

10. The lid of claim 9 wherein said top lid surface reflection minimizing shape extends continuously over said top lid surface linearly covering a plurality of wells.

11. The lid of claim 1 wherein said lid covers only a single row of wells of said multiwell plate.

12. The lid of claim 1 wherein said lid covers only a single column of wells of said multiwell plate.

13. The lid of claim 1 wherein said top surface is anti-reflection coated.

14. The lid of claim 1 further comprising a self-adjusting flexible plastic flange connected to one or more of said protruding elements which, when installed on a multiwell plate, is capable of sealing said well or wells against evaporation by deforming into a cone shape by making physical contact with the well sidewalls, regardless of plate-to-plate well diameter variability.

15. The lid of claim 1 further comprising a solid shoulder element adjacent to said bottom lid surface and each of said plurality of protruding elements wherein said shoulder element is angled such that a portion of it rests on the rim of said sample containing well and another portion of said shoulder protrudes into the sample containing well.

16. The lid of claim 1 further comprising removable grommet structures selected so as to adapt said lid structure to a selected multiwell plate, where said grommet structures are placed about said protruding elements and are capable of sealing said wells against evaporation.

* * * * *